US00PP19320P2

(12) United States Plant Patent
Jacobs

(10) Patent No.: US PP19,320 P2
(45) Date of Patent: Oct. 14, 2008

(54) ***ALSTROEMERIA* PLANT NAMED 'ZAPRILET'**

(50) Latin Name: *Alstroemeria hybrida*
Varietal Denomination: Zaprilet

(75) Inventor: Henricus Cornelius Maria Jacobs, Rijsenhout (NL)

(73) Assignee: Van Zanten Plants b.v., Hillegon (NL)

( * ) Notice: Subject to any disclaimer, the term of this patent is extended or adjusted under 35 U.S.C. 154(b) by 0 days.

(21) Appl. No.: 12/012,484

(22) Filed: Jan. 31, 2008

(51) Int. Cl.
*A01H 5/00* (2006.01)

(52) U.S. Cl. ..... Plt./309
(58) Field of Classification Search ..... Plt./309
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Alstroemeria* plant named 'Zaprilet', characterized by its upright and somewhat outwardly spreading plant habit; vigorous growth habit; red-colored flowers; and good garden performance.

1 Drawing Sheet

Botanical designation: *Alstroemeria hybrida.*
Cultivar denomination: 'Zaprilet'.

BACKGROUND OF THE INVENTION

The present invention relates to a new and distinct cultivar of *Alstroemeria* plant, botanically known as *Alstroemeria hybrida,* commercially used as a potted *Alstroemeria,* and hereinafter referred to by the name 'Zaprilet'.

The new *Alstroemeria* is a naturally-occurring whole plant mutation of the *Alstroemeria hybrida* cultivar Staprioxa, disclosed in U.S. Plant Pat. No. 14,075. The cultivar Zaprilet was discovered and selected by the Inventor as a single plant within a population of plants of the cultivar Staprioxa in a controlled environment in Rijsenhout, The Netherlands in May, 2002.

Asexual reproduction of the new *Alstroemeria* by rhizome divisions in a controlled environment in Rijsenhout, The Netherlands since September, 2002, has shown that the unique features of this new *Alstroemeria* are stable and reproduced true to type in successive generations.

SUMMARY OF THE INVENTION

The cultivar Zaprilet has not been observed under all possible environmental conditions. The phenotype may vary somewhat with variations in environment and cultural practices such as temperature and light intensity, without, however, any variance in genotype.

The following traits have been repeatedly observed and are determined to be the unique characteristics of 'Zaprilet'. These characteristics in combination distinguish 'Zaprilet' as a new and distinct cultivar of *Alstroemeria:*

1. Upright and somewhat outwardly spreading plant habit.
2. Vigorous growth habit.
3. Dark red-colored flowers.
4. Good garden performance.

Plants of the new *Alstroemeria* can be compared to plants of the parent, the cultivar Staprioxa. Plants of the new *Alstroemeria* differ primarily from plants of the cultivar Staprioxa in flower color as plants of the new *Alstroemeria* have darker red-colored flowers than plants of the cultivar Staprioxa. In addition, outer perianth segments of plants of the new *Alstroemeria* have more stripes than outer perianth segments of plants of the cultivar Staprioxa.

Plants of the new *Alstroemeria* can be compared to plants of the *Alstroemeria hybrida* cultivar Staprilene, disclosed in U.S. Plant Pat. No. 11,683. In side-by-side comparisons conducted in Rijsenhout, The Netherlands, plants of the new *Alstroemeria* differed from plants of the cultivar Staprilene in the following characteristics:

1. Plants of the new *Alstroemeria* were not as broad as plants of the cultivar Staprilene.
2. Plants of the new *Alstroemeria* had shorter leaves than plants of the cultivar Staprilene.
3. Plants of the new *Alstroemeria* had smaller flowers than plants of the cultivar Staprilene.
4. Plants of the new *Alstroemeria* and the cultivar Staprilene differed in flower color as plants of the cultivar Staprilene had pale yellow and white-colored flowers.

BRIEF DESCRIPTION OF THE PHOTOGRAPH

The accompanying colored photograph illustrates the overall appearance of the new *Alstroemeria,* showing the colors as true as it is reasonably possible to obtain in colored reproductions of this type. Colors in the photograph may differ slightly from the color values cited in the detailed botanical description which accurately describe the colors of the new *Alstroemeria.* The photograph comprises a side perspective view of a typical flowering plant of 'Zaprilet' grown in a container.

DETAILED BOTANICAL DESCRIPTION

The aforementioned photograph and following observations and measurements describe plants of the new *Alstroemeria* grown in Rijsenhout, The Netherlands during the winter in a glass-covered greenhouse in 14-cm containers. During the production of the plants, day temperatures ranged from 15° C. to 25° C., night temperatures ranged from 10° C. to 15° C. and light levels averaged 5,000 lux. Plants used for the photograph and description were about four months from planting. Color references are made to The Royal Horticultural Society Colour Chart, 1995 Edition, except where general terms of ordinary dictionary significance are used.

Botanical classification: *Alstroemeria hybrida* cultivar Zaprilet.

Parentage: Naturally-occurring whole plant mutation of the *Alstroemeria hybrida* cultivar Staprioxa, disclosed in U.S. Plant Pat. No. 14,075.

Propagation:

*Type.*—By rhizome divisions.

*Time to produce a rooted young plant, summer.*—About 40 days.

*Time to produce a rooted young plant, winter.*—About 60 days.

*Root description.*—Fibrous, fleshy, thick; close to 155D, in color.

*Rooting habit.*—Freely branching; moderately dense.

*Rhizomes.*—Shape: Elongate; rounded. Length: About 10 cm to 30 cm. Diameter: About 3 mm to 10 mm. Texture: Smooth. Color: Close to 155D.

Plant description:

*Plant habit.*—Upright and somewhat outwardly spreading plant habit. Freely branching habit with about 10 to 15 primary branches developing per plant, dense and bushy appearance. Vigorous growth habit.

*Plant height.*—About 20 cm to 30 cm.

*Plant diameter* (*spread*).—About 30 cm to 40 cm.

Flowering stem description:

*Aspect.*—Upright to somewhat outwardly spreading.

*Length.*—About 10 cm to 20 cm.

*Diameter.*—About 3 mm to 8 mm.

*Internode length.*—About 0.5 cm to 1.5 cm.

*Strength.*—Strong.

*Texture.*—Smooth, glabrous.

*Color.*—146B.

Foliage description:

*Appearance.*—Leaves asymmetrical; sessile.

*Length.*—About 6 cm to 9 cm.

*Width.*—About 2 cm to 3 cm.

*Shape.*—Elliptic.

*Apex.*—Acute.

*Base.*—Attenuate.

*Margin.*—Entire.

*Texture, upper and lower surfaces.*—Smooth, glabrous.

*Venation pattern.*—Parallel.

*Color.*—Developing and fully developed foliage, upper surface: Close to 137C; venation, close to 137C. Developing and fully developed foliage, lower surface: Close to 137C; venation, close to 137C.

Flower description:

*Flower type and habit.*—Single cup-shaped flowers arranged in compound umbels. Flowers face mostly upright. Perianth segments separate. Freely and continuously flowering. Flowers not persistent.

*Natural flowering season.*—Flowering continuous during the spring in The Netherlands.

*Fragrance.*—None detected.

*Flower longevity on the plant.*—About four weeks.

*Flower buds* (*showing color*).—Length: About 3.5 cm to 4.5 cm. Diameter: About 1.5 cm to 2 cm. Shape: Roughly ovoid. Color: Close to 46A.

*Umbel height.*—About 9 cm to 12 cm.

*Umbel diameter.*—About 10 cm to 14 cm.

*Number of flowers per umbel.*—About two to ten.

*Flower diameter.*—About 5.5 cm to 6.5 cm.

*Flower length* (*height*).—About 6.5 cm to 7 cm.

*Flower depth.*—About 5 cm to 6 cm.

*Perianth.*—Arrangement: Six arranged in two whorls, each whorl with two lateral and one median segments. Size, outer perianth: Length, lateral segments: About 4.5 cm to 5.5 cm. Width, lateral segments: About 3.2 cm to 3.6 cm. Length, median segment: About 4.5 cm to 5.5 cm. Width, median segment: About 3.2 cm to 3.6 cm. Size, inner perianth: Length, lateral segments: About 5 cm to 5.5 cm. Width, lateral segments: About 1.8 cm to 2.2 cm. Length, median segment: About 4.5 cm to 5.5 cm. Width, median segment: About 1.8 cm to 2.1 cm. Shape, outer perianth, lateral and median segments: Obovate. Shape, inner perianth, lateral and median segments: Oblanceolate. Apex, outer perianth, lateral and median segments: Embedded pointed. Apex, inner perianth, lateral and median segments: Wishbone-shaped. Base, outer and inner perianths, lateral and median segments: Attenuate. Margin, outer and inner perianths, lateral and median segments: Entire; weakly undulate. Texture, outer and inner perianths, lateral and median segments: Smooth, glabrous. Color, outer perianth: When opening and fully opened, lateral and median segments, upper surface: 46A; at the apex, close to 144A; stripes, close to 183A. When opening and fully opened, lateral and median segments, lower surface: 46A; at the apex and midvein, close to 144A. Color, inner perianth: When opening and fully opened, lateral and median segments, upper surface: 46A; towards the center and base, 17B; stripes, close to 183A. When opening and fully opened, lateral and median segments, lower surface: 46A; towards the center, 17B; at the base, between 30C and 35C.

*Peduncles.*—Length: About 1 cm to 3 cm. Diameter: About 2 mm to 3 mm. Strength: Strong. Angle: About 20° to about 30° from vertical. Texture: Smooth, glabrous. Color: Close to 146C.

*Reproductive organs.*—Stamens: Quantity per flower: Six. Filament color: Close to 48A. Anther shape: Elliptic. Anther length: About 8 mm. Anther diameter: About 2 mm. Anther color: Close to 152D. Pollen amount: Scarce. Pollen color: Close to 152D. Pistils: Quantity per flower: One. Style length: About 4 cm to 4.5 cm. Style color: Close to 47B. Stigma color: Close to 47B. Ovary color: 146B.

*Fruit/seed.*—Fruit and seed development has not been observed.

Disease/pest resistance: Plants of the new *Alstroemeria* have not been observed to be resistant to pathogens and pests common to *Alstroemeria*.

Garden performance: Plants of the new *Alstroemeria* have been observed to have good garden performance and to tolerate wind, rain and temperatures from about −5° C. to about 40° C.

It is claimed:

1. A new and distinct *Alstroemeria* plant named 'Zaprilet' as illustrated and described.

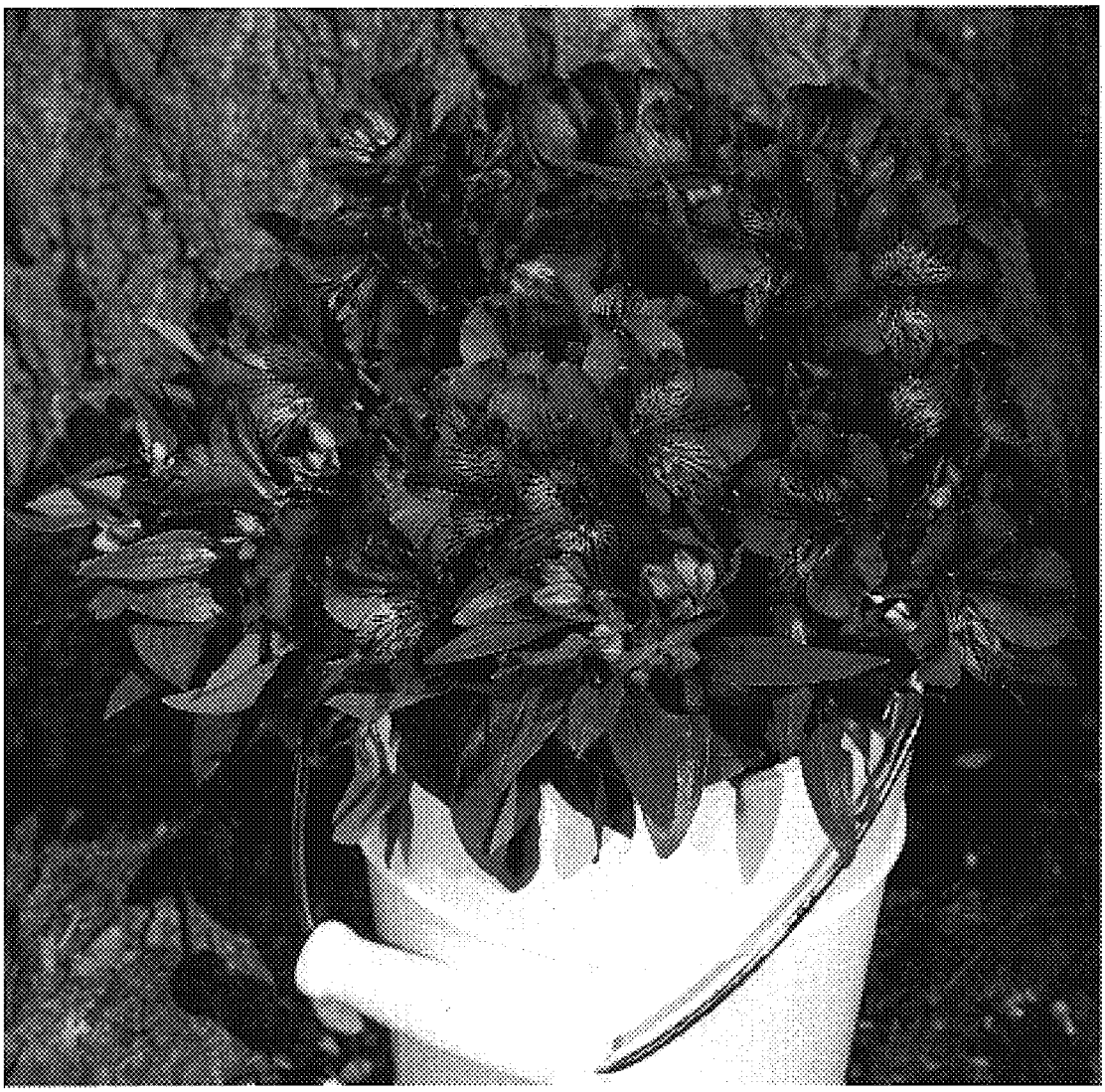

* * * * *